United States Patent [19]
Sanders et al.

[11] Patent Number: 5,766,605
[45] Date of Patent: Jun. 16, 1998

[54] TREATMENT OF AUTONOMIC NERVE DYSFUNCTION WITH BOTULINUM TOXIN

[75] Inventors: Ira Sanders; Christopher M. Shaari. both of New York, N.Y.

[73] Assignee: Mount Sinai School of Medicine of the City University of New York, New York, N.Y.

[21] Appl. No.: 228,132

[22] Filed: Apr. 15, 1994

[51] Int. Cl.$^6$ .................................................. A61K 35/74
[52] U.S. Cl. ............................... 424/239.1; 424/236.1; 424/45; 424/434; 424/78.02; 514/937; 514/944; 514/826
[58] Field of Search .......................... 424/45, 434, 236.1, 424/234.1, 78.05, 78.02, 239.1; 514/937, 944, 925, 826

[56] References Cited

PUBLICATIONS

Vita, G. et al. (1987). Arch. Neurol. 44:202–206.
Molgo, J. et al. (1990). J. Physiol. Paris 84:152–166.
Girlanda, P. et al. (1992). J. Neurol. Neurosurg. Psychiatry 55:844–845.
Ambache (1951). J. Physiology 113: 1–17.
Pasricha PJ, Ravich WJ, Hendrix TR, Sostre, S, Jones B, Kalloo AN. Intrasphincteric Botulinum Toxin For The Treatment of Achalasia. N. Engl. J. Med. 1995;332:774–778.
Pasricha PJ, Ravich WJ, Hendrix TR, Sostre S, Jones B, Kalloo AN. Treatment of Achalasia with Intrasphincetric Injection of Botulinum Toxin. Ann. Intern. Med. 1994;121:590–591.
Pasricha PJ, Ravich WJ, Kalloo AN. Effects of Intrasphincetric Botulinum Toxin on the Lower Esophageal Sphincter in Piglets. Gastroenterology 1993;105:1045–1049.
Ferrari AP, Siqueira ES, Brant CQ. Treatment of Achalasia in Chaga's Diesease With Botulinum Toxin. N. Engl. J. Med. 1995;332:824–825.
Bushara KO, Park DM. Botulinum Toixn and Sweating. J. Neurol. Neurosurg. Psychtr. 1994;57(11):1437–1438.
Schantz EJ, Johnson EA. Properties and Use of Botulinum Toxin and Other Microbial Neurotoxins in medicine. Microbiological Reviews. 1992;56:80–99.
Gargarosa EJ. Botulism. In PD Hoeprich, ed., Infectious Diseases, Harper and Row, Hagerstown, Md., 1972.
Jankovic J, Brin MF. Therapeutic uses of botulinum toxin. NEJM. 1991;324:1186–1194.
Malcomson KG. The vasomotor activities of the nasal mucous membrane. J Lar Otol 1959;73:73–98.
Krajina Z. Critical review of Vidian neurectomy. Rhinology 1989;27:271–276.
Eccles R, Wilson H. The parasympathetic secretory nerves of the nose of the cat. J. Physiol 1973;230:213–223.
Laurikainen E, Koulu M, Kaila T, Scheinin M, Isalo E. Evaluation of the systemic anticholinergic activity of nasally administered ipratropium bromide. Rhinology 1988;26:133–138.
Mygind N, Borum P. Effect of a cholino–ceptor antagonist in the nose. Eur J Respir Dis 1983;64 (suppl 128):167–174.

Golding–Wood PH. Pathology and surgery of the chronic vasomotor rhinitis. J Lar Otol 1962:76;969–977.
Malm L. Stimulation of sympathetic nerve fibres to the nose in cats. Acta Otolaryngol 1973;75:519–526.
Uddman R, Alumets J, Densert O, Hakanson R, Sundler F. Occurrence and distribution of VIP nerves in the nasal mucosa and tracheobronchial wall. Acta Otolaryngol 1978;86:443–448.
Scott AB, Kennedy RA, Stubbs MA. Botulinum A toxin injection as a treatment for blepharospasm. Arch Opthalmol 1985;103:347–350.
Scott AB. Botulinum toxin injection of eye muscles to correct strabismus. Trans Am Ophthal Soc. 1981;79:734–770.
Black JD, Dolly JO. Selective location of acceptors for botulinum neurotoxin A in the central and peripheral nervous systems. Neuroscience. 1987;23:767–779.
Ambache N. The peripheral action of Cl. botulinum toxin. J Physiol. 1949;108:127–141.
Carpenter FG. Motor responses of the urinary bladder and skeletal muscle in botulinum intoxicated rats. J Physiol. 1967;188:1–11.
Marier SH, Putney JW, Van de Walle CM. Control of calcium channels by membrane receptors in the rat parotid gland. J. Physiol. 1978;279:141–151.
Aub DL, McKinney JS, Putney JW. Nature of the receptor–regulated calcium pool in the rat parotid gland. J. Physiol. 1982;331:557–565.
Ekstrom J, Tobin G. Secretion of protein from salivary glands in the ferret in response to vasoactive intestinal peptide. J. Physiol. 1989;415:131–141.
Putney JW. Identification of cellular activation mechanisms associated with salivary secretion. Ann. Rev. Physiol. 1986;48:75–88.
Nakahari T, Miyamoto M, Yoshida H, Tanaka H, Imai Y. Continuous Measurements of Tissue Impedance during Secretion in Dog Submandibular Gland. Jpn J Physiol. 1988;38:699–712.
Dohi T, Yamaki H, Morita K, Kitayama S, Tsuru H, Tsujimoto A. Calcium dependency of adrenergic and muscarinic cholinergic stimulation of mucin release from dog submandibular gland cells. Archs Oral Biol. 1991;36:443–449.
Krajina Z, Harvey JE, Ogura JH. Experimental vasomotor rhinitis. Laryngoscope 1972;82:1068–1073.

(List continued on next page.)

*Primary Examiner*—Raj Bawa
*Attorney, Agent, or Firm*—Baker & Botts, LLP

[57] ABSTRACT

There is disclosed according to the present invention a method for the control of autonomic nerve function in a mammal comprising administering a therapeutically effective amount of botulinum toxin to the mammal. Preferred embodiments include administering the toxin to control the function of an autonomic nerve which contributes to at least one symptom of rhinorrhea, otitis media, excessive salivation, asthma, COPD, excessive stomach acid secretion, spastic colitis or excessive sweating.

18 Claims, 8 Drawing Sheets

OTHER PUBLICATIONS

Millonig AF, Harris HE, Gardner WJ. Effect of autonomic denervation on nasal mucosa. Arch Otolaryngol 1949;86:359–368.

Martling CR, Anggard A, Lundberg JM. Non-cholinergic vasodilation in the tracheobronchial tree of the cat induced by vagal nerve stimulation. Acta Physiol Scand 1985;125:343–346.

Anggard A. The effects of parasympathetic nerve stimulation on the microcirculation and secretion in the nasal mucosa of the cat. Acta Otolaryngol 1974;78:98–105.

Cauna N. Blood and nerve supply of the nasal lining. In: Proctor DF, Andersen I, eds. The nose. Upper airway physiology and the atmospheric environment. Amsterdam. Elsevier Biomedical Press, 1982;45–69.

Tos M. Distribution of mucus producing elements in the respiratory tract. Differences between upper and lower airway. Eur J Respir Dis 1983 (suppl 128):269–279.

Krajina M. and Poljak Z. Reaction of Nasal Mucosa in Rabbits after Cervical Sympathectomy. Acta oto–laryng.53, pp. 116–121.

ELECTRICAL STIMULATION

■ CONTROL
□ 50 U TYPE D TOXIN

FIG. 6A

GRAMS/MINUTES vs MINUTES (0–10)

TREATMENT OF AUTONOMIC NERVE DYSFUNCTION WITH BOTULINUM TOXIN

BACKGROUND OF THE INVENTION

The present invention is directed to the use of botulinum toxin to block parts of the autonomic nervous system for clinically beneficial effects.

Botulinum toxin is produced by *Clostridium botulinum* in at least seven distinct serotypes, designated A-G (1). The toxin acts at cholinergic nerves to inhibit the release of acetylcholine, producing local chemical denervation. Because the seven types are antigenically distinct they have different anticholinergic potencies on cholinergic motor nerves (1). With respect to motor nerves, type A toxin has the greatest anticholinergic effect at the neuromuscular junction, followed by types E then B (2).

Heretofore, botulinum toxin, i.e., botulinum toxin A, has been used to treat various motor nerve disorders. For example botulinum toxin injections are now considered treatment of choice for spasmodic dysphonia, blepharospasm, torticollis, focal hand dystonias and others (3). The use of type A toxin was approved in 1991 by the Food and Drug Administration as injectable therapy for strabismus and blepharospasm.

While botulinum toxin has been used to denervate cholinergic motor nerves, it has not been used with respect to autonomic nerves.

An example of autonomic nerve function is with respect to the patency of the nasal airway, which is regulated by the autonomic nervous system. Sympathetic activity decreases nasal airway resistance by constricting nasal capacitance vessels and venous sinusoids, and parasympathetic activity produces nasal mucus from submucosal seromucinous glands. Dysfunction of either of these two systems can give rise to the sensation of nasal blockage.

Nasal mucus is composed of 96 percent water and about 3 percent mucin (4). Excessive parasympathetic activity produces a copious flow of clear, watery secretions. This is a well-known feature of vasomotor rhinitis (5), and has been demonstrated in cats following direct electrical stimulation of the Vidian nerve (4,6). Therapeutic efforts to decrease rhinorrhea in humans have attempted to either sever the parasympathetic nerve supply through Vidian neurectomy (5), or chemically block the mucosal receptors for acetylcholine using the short-acting, topical atropine analog ipratropium (7). Either therapy produces only partial relief of symptoms (5,8).

Vidian neurectomy was first introduced in the early 1960's (9). The rational of cutting this nerve was to interrupt the hyperactive parasympathetic secretomotor fibers (4). However, by doing this, sympathetic fibers were sectioned as well. Regeneration of the parasympathetic fibers was suggested as causing the long-term return of rhinorrhea following Vidian neurectomy (10). The partial response to anticholinergic inhalation agents (ipratropium) has been attributed to the existence of non-cholinergic mediators, such as vasoactive intestinal peptide (VIP), that cause rhinorrhea (11). Today, inhalational agents are considered first-line therapy for vasomotor rhinitis, but require application up to four times daily (8). Vidian neurectomy is reserved for patients refractory to conservative therapy (5). Thus as a practical matter, there is no viable long-lasting effective therapy for vasomotor rhinitis.

As noted above, the nature and effect of botulinum toxin, particularly on motor nerves, have been studied. Botulinum toxin is a neurotoxin that inhibits the release of acetylcholine from the presynaptic nerve terminal (12). Following intramuscular injection, its paralytic effects last between 2–6 months (3). Normally, following stimulation of a nerve, the release of acetylcholine from the presynaptic nerve terminal requires the influx of extra-cellular calcium into the presynaptic terminal (13). Botulinum exerts its effect by blocking or interfering with the utilization of this extracellular calcium pool (1), thus the release of acetylcholine vesicles is inhibited.

Previous anatomic and physiologic studies have demonstrated that autonomic nerves are susceptible to botulinum toxin, but only in highly lethal doses. Black and Dolly (14) demonstrated that I-125 radiolabelled botulinum A toxin binds to cholinergic nerves in the mouse myenteric plexus. Ambache (15) injected lethal doses of non-purified type A toxin into the orbits of rats and noted that the iris failed to react to light or direct oculomotor nerve stimulation just prior to death. He concluded that parasympathetic nerves in the iris were chemically denervated by the toxin. Conversely, Carpenter (16) failed to produce consistent blockage of parasympathetically innervated viscera following intravenous injections of lethal doses of type A toxin into rabbits. However, rabbits which were overdosed with equivalent doses of type D toxin demonstrated evidence of parasympathetic paralysis (mydriasis and urinary retention) well before there was obvious sign of skeletal muscle paralysis. He concluded that parasympathetic postganglionic fibers were more vulnerable to type D toxin than to type A toxin.

SUMMARY OF THE INVENTION

According to the present invention, a variety of autonomic nerve targets, modes of administration of botulinum toxin, and resultant beneficial clinical effects are contemplated. For example, rhinorrhea (post nasal drip) may be effectively treated either by topical application of botulinum toxin onto the nasal mucosa or injection into the sphenopalatine ganglion. It is further contemplated that the use of nasal sprays or drops would be effective.

Otitis media could be treated by the transtympanic injection of botulinum toxin.

Where decreased salivation is sought (e.g. in patients with cerebrovascular accidents, ALS, myasthenia gravis, bulbar palsy, and vagal dysfunction), botulinum toxin may be administered to the salivary glands.

In asthma or COPD patients, treatment by aerosol delivery or transbronchial injection of botulinum toxin will relax the bronchial muscles.

The oral ingestion of botulinum toxin can be utilized to decrease the secretion of stomach acid.

Relief from spastic colitis is further contemplated by administering botulinum toxin, either by enema or suppositories.

Patients experiencing excessive sweating could experience relief by the topical application or intradermal injection of botulinum toxin.

Although botulinum toxin A is presently used and approved for the treatment of motor nerve disfunction, the present invention encompasses the treatment of autonomic nerve functions or dysfunctions with any of the seven known types of botulinum toxin (A-G), as well as the closely related toxins produced by the *Clostridium butyricum* and *beratti*.

DESCRIPTION OF THE PREFERRED EMBODIMENTS

The efficacy of botulinum toxin as a beneficial pharmaceutical agent to control or treat autonomic nerve function or dysfunction is demonstrated by the following examples.

Example I

The production of saliva following cholinergic stimulation has been explored in detail in rodents (17,18,19,20). Salivary cells respond to carbechol (a direct, cholinergic agonist) stimulation in a characteristic biphasic manner: an initial transient production of saliva occurs, lasting 1–2 minutes, that is mediated by intracellular calcium stores (18). Only 2–3 minutes of rest following stimulation are needed to replenish these intracellular calcium stores, after which normal secretory function is restored. This initial phase is followed by a sustained (or slowly falling) phase that requires extracellular calcium (18,20). In the absence of extracellular calcium, only the early transient phase is obtained following cholinergic stimulation. These results were originally described in rodents, but were also noted in the canine submandibular gland (21,22).

Acinar cells are similar to nerve cells in that both require extracellular calcium to maintain prolonged function. Since botulinum toxin normally blocks these calcium channels on nerve tissue, it was hypothesized that the toxin may also act on acinar cells to block the influx of extracellular calcium. Thus, botulinum toxin could: 1) Paralyze the lingual nerve, 2) Bind to calcium channels on acinar cells, rendering them non-functional, or 3) Poison the acinar cells by some other mechanism. A simple way to determine whether botulinum acted on the acinar cells was to stimulate the toxin-injected glands directly with systemic bethanechol (a cholinergic agonist). If botulinum acted directly on the acinar cells to block calcium channels, bethanechol stimulation would produce an initial production of saliva, but not a sustained production of saliva. If botulinum poisoned the acinar cells directly, neither electrical nor direct cholinergic stimulation would produce saliva.

This example was directed to the anticholinergic effects of purified botulinum toxin types A and D. Non-lethal doses were used. These types were chosen because type A is readily available and FDA approved (1), whereas type D has more potent autonomic rather than cholinergic motor effects (16). The purpose was to determine 1) whether parasympathetic nerve paralysis occurred, 2) whether parasympathetic nerves were more vulnerable to type D or type A toxin, and 3) whether the toxin acted directly on the acinar cells, either functionally or lethally.

The effect of intraglandular injections of botulinum toxin types A and D was studied in a total of 20 male mongrel dogs (18–20 kg).

For control purposes, to determine whether each submandibular gland of a dog produced equal volumes of saliva when the lingual nerves were identically electrically stimulated, 1 dog was anesthetized with pentobarbital (64.8 mg/2.2 kg) and the right lingual nerve was identified then stimulated. Saliva was collected, then the same procedure was performed on the left side.

The procedure to identify the lingual nerve/submandibular gland junction will be described here. A skin incision was made parallel to the body of the mandible, dividing skin and fascia to expose the mylophyoid muscle. The mylohyoid muscle was carefully divided craniocaudally to reveal the underlying trigeminal (V2) trunk and submandibular gland ducts. The lingual nerve was consistently identified as branching caudally from the trigeminal trunk towards the submandibular gland. The lingual nerve was dissected free and a bipolar hook electrode was placed around it. The salivary ducts were transected anteriorly in the same field for collecting saliva. Bipolar electrical stimulation was delivered at 4 mAmp, 20 Hz for 10 minutes. During stimulation, the saliva was collected and weighed.

Also for purposes of establishing control data, and to determine the percentage of the saliva that was cholinergically mediated, the right gland of one dog was stimulated as above and served as the dogs inherent control. The left side was exposed, then 1 mg of atropine was pushed intravenously. Five minutes were allowed for atropine to take effect, then the left lingual nerve was electrically stimulated and saliva collected. These results represented full cholinergic blockade to which botulinum-injected glands could be compared.

Control data was further provided by comparing the weights of saliva produced by two different cholinergic stimuli (electrical stimulation of the lingual nerve versus exposure of the gland to intravenous bethanechol), the right lingual nerve of one dog was electrically stimulated and saliva collected. Next, the left salivary ducts were exposed and 5 mg bethanechol was pushed i.v. Saliva was collected from the left side for 10 minutes, weighed and compared to the electrically-stimulated right side.

Then, in order to determine the effect of botulinum toxin on the neuroglandular junction, the following general procedure was followed. Each experimental (i.e., non-control) dog underwent two separate operations. In the first operation (day 1), the left submandibular gland of each dog was injected with toxin. An equivalent volume of normal saline was injected into the right gland to serve as control. The second operation took place on day six. The six day time period was chosen since the toxin takes at least 24–48 hours to produce weakness when injected into skeletal muscle; the time to onset of weakness with autonomic nerves has not been determined, thus six days was allowed for effect. Each dog was reanesthetized and the lingual nerve was exposed and electrically stimulated (3 mAmp, 20 Hz, 10 minutes). Saliva was collected from both the control side and the toxin injected side and weighed. The weight of saliva was a more accurate measurement than volume of saliva, as bubbles often made volume measurements difficult. Thus, only weights were recorded after the sixth dog. Furthermore, volume and weight were usually one 1–2% different.

In order to test type A toxin, eight dogs were used. On day one, each dog was given a short-acting bolus of pentobarbital (64.8 mg/2.2 kg). Increasing amounts of type A botulinum toxin (Oculinum Inc., Berkeley, Calif.) were injected into the left submandibular gland of three dogs under direct visualization. The lyophilized toxin was reconstituted with non-reserved saline to a concentration of 1.25 u/0.1 cc immediately prior to injection. The right gland of each dog was injected with equivalent volumes of saline. Two dogs received 10 units each, 2 dogs 30 units each, 2 dogs 50 units each, and 2 dogs 70 units each. All dogs were fed a regular diet following surgery.

On day 6, each dog was reanesthetized with pentobarbital intravenously as above. The lingual nerves of each dog were electrically stimulated and saliva collected. The weight of saliva was compared 1) between sides (saline vs. toxin) and 2 among dogs injected with different doses of type A toxin. In one dog injected with 10 unites, flow rates were compared between control and experimental sides.

For type D toxin, ten dogs were used. Toxin was supplied by WAKO Chemical (Richmond, Va.). Immediately prior to use, the buffered toxin was thawed and then diluted in normal saline to 50 units/1.0 cc. On day one, five dogs were injected with 50 units type D toxin, and five dogs were injected with 100 units type D toxin into the left submandibular gland under direct visualization. These doses were chosen since the relative potency of types A and D toxin on the neuroglandular junction is unknown. In order to determine whether paralysis occurred at simple reference values (50 and 100 units), equivalent volumes of saline were injected into the right gland of each dog. All dogs were fed a regular diet following surgery.

On day six, the lingual nerves of each dog were stimulated and saliva collected. In two dogs injected with 50 units, flow rates were compared between control and experimental sides. The weight of saliva was compared 1) between sides (saline vs. toxin) and 2) among dogs injected with different doses of type D toxin. Note that this protocol does not serve to localize the effect of botulinum on the neuroglandular junction.

In order to localize the effect of botulinum toxin, a bethanechol challenge was undertaken. As noted above, the flow rates of one dog treated with 10 units type A toxin and two dogs treated with type D toxin were recorded during electrical stimulation. These dogs were then subject to bethanechol challenge. One hour following electrical stimulation, 5 mg of bethanechol was pushed intravenously to produce systemic cholinergic stimulation. Saliva was collected from both saline and toxin-injected sides simultaneously at 1 minute intervals for 10 minutes. The saline-injected right gland served as inherent control to the toxin-injected left gland. Weights of saliva were compared in each dog between the saline and toxin-injected sides.

The results of the above example are summarized as follows.

With respect to the control studies, equivalent stimulation of normal left and right lingual nerves produced similar weights of saliva. An inherent difference of 8% (12.63 vs 11.50 gm) existed between sides (FIG. 1). Intravenous injection of 1 mg atropine reduced the weight of saliva by 76% (20.54 vs 7.61 gm, FIG. 1). Ten minutes of electrical stimulation of a normal gland produced 12.99 gms of saliva. Ten minutes of bethanechol stimulation recorded from the opposite gland produced only 3.08 gms of saliva. Hence, in an normal gland, bethanechol stimulation produced only about 28% of the amount of saliva produced by electrical stimulation. FIG. 1 represents final volume, FIG. 2 represents flow rates between electrical vs bethanechol stimulation.

The results of the tests of botulinum toxin (A and D) on the neuroglandular junction were as follows. For type A toxin, all dogs survived initial surgery. The raw data for dogs injected with type A toxin is depicted in FIG. 3. In general, type A toxin failed to reduce the neurally-evoked production of saliva in six of eight dogs. In two dogs, injections of 30 and 50 units reduced the production of saliva by 33.1% and 90% respectively. These results were not reproducible. The average percent decrease for 10,30,50 and 70 units type A toxin were 9%, 22%, 49% and 16% respectively. Due to the small number of animals in each dose group (N=2) no conclusions can be drawn regarding dose effect of type A toxin.

For type D toxin, all dogs survived initial surgery. The raw data for dogs injected with 50 and 100 units of type D toxin are depicted in FIGS. 4 and 5 respectively. In general, eight out of 10 dogs injected with either 50 or 100 units type D toxin showed a marked reduction in saliva production. The average percent decrease for 50 and 100 units type D toxin were 56% and 64% respectively. Statistically significance was achieved in both groups: 0.0115/8 for 50 units, and 0.00622 for 100 units ($p<0.05$).

The results showing the effect of botulinum on acinar cells were as follows.

Bethanechol challenge produced nearly equal flow rates and weights of saliva from control and toxin-injected glands in all three dogs. FIG. 6 represents the flow rates of one dog injected with 50 units type D toxin, stimulated electrically then, one hour later, with bethanechol.

In the above experiment, it was demonstrated that botulinum toxin types A and D reduced the neurally evoked production of saliva from canine submandibular glands. Although comparable doses were not given, type D toxin appeared more potent and yielded more consistent anticholinergic effects. Systemic atropine, representing complete cholinergic blockage, reduced the production of saliva by 76%. Thus 24% was probably mediated by non-cholinergic neurotransmitters that would not be affected by botulinum toxin either.

Of the eight dogs injected with type A toxin, six failed to show an anticholinergic effect from the toxin. Only two dogs injected with medium doses of type A toxin (30 and 50 units) showed a marked decrease in saliva production. This could represent either individual susceptibility to botulinum toxin, or, more likely, technical error when stimulating the lingual nerve on the experimental side. Due to the number of animals in each dose group, no statistical analysis can be performed nor conclusions drawn regarding dose effect for type A toxin.

Injections of either 50 or 100 units type D toxin into the submandibular glands marked reduced the production of saliva. The average decrease in weight was 56% and 64% respectively. Statistical significance was achieved for both groups, with the greatest significance seen at 100 units of toxin (0.00622, with $p<0.05$).

A further purpose of this experiment was to determine whether botulinum's effect was mediated through parasympathetic nerve paralysis only, or through acinar cell toxicity as well. The bethanechol challenge served to differentiate the mechanism of action. It was hypothesized that if botulinum acted on acinar cells to block calcium channels, stimulation of the cells with a direct elevation of saliva flow would be mediated by intracellular stores, but the sustained response would cease since extracellular calcium could not enter the cell. This pattern was not observed. Instead, bethanechol produced an initial and equal burst of saliva from control and experimental glands, then produced equal and sustained amounts of saliva from control and experimental glands for 10 minutes. FIG. 6 graphically demonstrates this. This suggested that the calcium channels on the acinar cells were not blocked by botulinum toxin. Moreover, because toxin-injected glands produced similar flow rates and weights of saliva as normal glands following bethanechol stimulation, the acinar cells were probably not directly poisoned by botulinum toxin.

Example II

Dog studies indicate that injecting toxin into salivary glands may reduce sialorrhea in neurologically impaired patients, or reduce saliva production in patients with salivary gland obstruction. Intraoperative injections of toxin into salivary glands will help prevent postoperative salivary fistulas of head and neck reconstruction. Although injections of type A toxin would seem most feasible (already FDA approved), type A was minimally effective in reducing salivary production. Conversely, it appeared that the nerve terminals were susceptible to the presynaptic action of type D toxin at doses of 50 and 100 units. Strict comparisons between types A and D toxin cannot be made from preliminary data because different concentrations and doses of types A and D toxin were used. Thus parasympathetic postganglionic neurons that innervate the canine submandibular glands are susceptible to the anticholinergic effect of botulinum toxin types A and D. Type D toxin appears to have a greater effect in reducing the neurally-evoked production of saliva in dogs. Neither type A nor D toxin appeared to effect the acinar cells directly.

Example III

Botulinum toxin may also benefit patients suffering other forms of autonomic dysfunction, including Frey's syndrome, asthma or rhinorrhea. Botulinum toxin was effective in reducing electrically-evoked rhinorrhea in dogs. Surprisingly, although type A toxin had little effect on the lingual nerve/submandibular gland junction, type A toxin reduced rhinorrhea an average 41% in three of four dogs exposed to intranasal botulinum. These results suggest that different autonomic systems may have different susceptibilities to the toxin.

Example IV

From Example I, it was shown that the intranasal application of botulinum toxin could be an effective long-term therapy for vasomotor rhinitis. In order to further test this hypothesis, the following experiment was conducted with respect to type A toxin.

As a general matter, six male mongrel dogs were used (18–22 kg). In order to develop a model to quantify the production of nasal secretions following electrical stimulation of the sphenopalatine ganglion; each dog was sedated with intravenous pentobarbital (64 mg/2.2 kg), endotracheally intubated and laid prone on the operating table. Surgical towels were placed under the neck to create a 45 degree slope from the nasopharynx to nostrils, facilitating the collection of secretions from the nostrils. The sphenopalatine ganglion was stimulated with a bipolar needle electrode of 0.46 mm diameter (Medelec International, Old Woking, Surrey) as follows. With the dog's mouth stented open with a bite-block, the needle was gently inserted into the greater palatine canal advanced toward the sphenopalatine ganglion. Previous studies on canine cadaver heads revealed this distance to be about 1.5–2.0 cm into the canal. The location of the ganglion was physiologically confirmed by applying electrical stimulation (6 mAmp, 50 Hz) after the needle was about 1.5 cm into the canal, then advancing the needle until ipsilateral lacrimation was noted. In general, deviations from this end point by only 1–2 mm stopped the production of tears and nasal secretion. Once the ganglion was identified, electrical stimulation was applied for 10 minutes, and nasal secretions collected.

Secretions were collected from the nose by placing a small suction catheter in the ipsilateral vestibule. No attempt was made to place the suction into the nasal cavity, for stimulation of the trigeminal nerve by the catheter caused reflex rhinorrhea. The suction catheter was connected to a suction Erlenmeyer flask so that secretions could be collected and weighed at the end of stimulation. Controls were established to demonstrate that each side of a dog's nasal cavity produced an equal amount of secretion when identically stimulated.

Once this model was established, the next objective was to determine whether botulinum-exposed nasal mucosa produced less secretion than saline-exposed nasal mucosa following electrical stimulation of the sphenopalatine ganglion. The experimental dogs were subjected to two separate procedures. On day one, type A botulinum toxin (Oculinum Inc. Berkeley, Calif.) was introduced into the left nasal cavity, and an equivalent volume of saline into the right. The nasal packing was removed after one hour and the dogs awakened. Because the toxin normally takes 24–48 hours to take effect (3), there was a six day delay before stimulating the sphenopalatine ganglia to produce rhinorrhea. On day six, both ganglia were stimulated and weights of the nasal secretion were collected and compared.

On a more specific level, in order to establish a control two dogs were anesthetized. In each dog, the right then left sphenopalatine ganglia were identically stimulated. Secretions were collected then compared between sides. It was predicted that the weights would be equal.

One hour following the above stimulation, 1 mg of atropine was injected intravenously. The right sphenopalatine ganglion was again electrically stimulated for 10 minutes and secretions collected. Any decreased weight of rhinorrhea represented cholinergic blockage. Previous work had demonstrated that the full secretory potential of the nasal mucosa was restored following 20 minutes of rest.

In order to determine the effect of type A toxin, four dogs were each anesthetized. On day one, a pentobarbital bolus (64.8 mg/5 lb) was given intravenously to temporarily sedate the dogs. The right and left nasal cavities were each decongested with ¼% neosynephrine (5 drops) and sprayed with 4% xylocaine spray. Next, 50 units of type A botulinum toxin (total volume 4 cc, concentration 1.25 units/0.1 cc) was soaked into 10 inches of sterile 1" gauze packing then layered into the left nasal cavity to cover the entire nasal mucosa. The botulinum toxin was received in lyophilized form and reconstituted with preserved normal saline immediately prior to use. Similarly, 10 inches of saline-soaked gauze packing was placed into the right nasal cavity. The packs were let in place for one hour to allow maximal absorption of toxin to the mucosa. After one hour, the packs were removed. The dogs awoke after about four hours.

On day six, the dogs were reanesthetized with pentobarbital (64 mg/5 lb), endotracheally intubated and placed prone on the operating table as previously described. The right then left sphenopalatine ganglia were sequentially stimulated as described. Secretions were collected from each nasal cavity then compared between toxin-exposed and saline-exposed sides.

Figure 1:
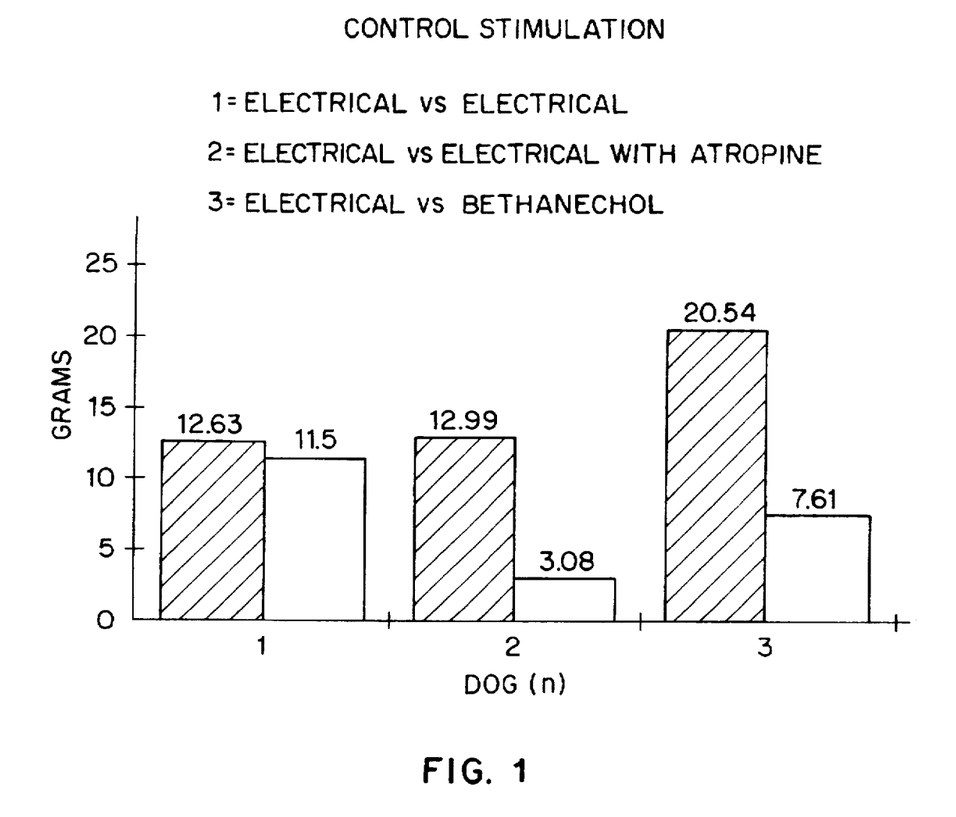
Figure 2:
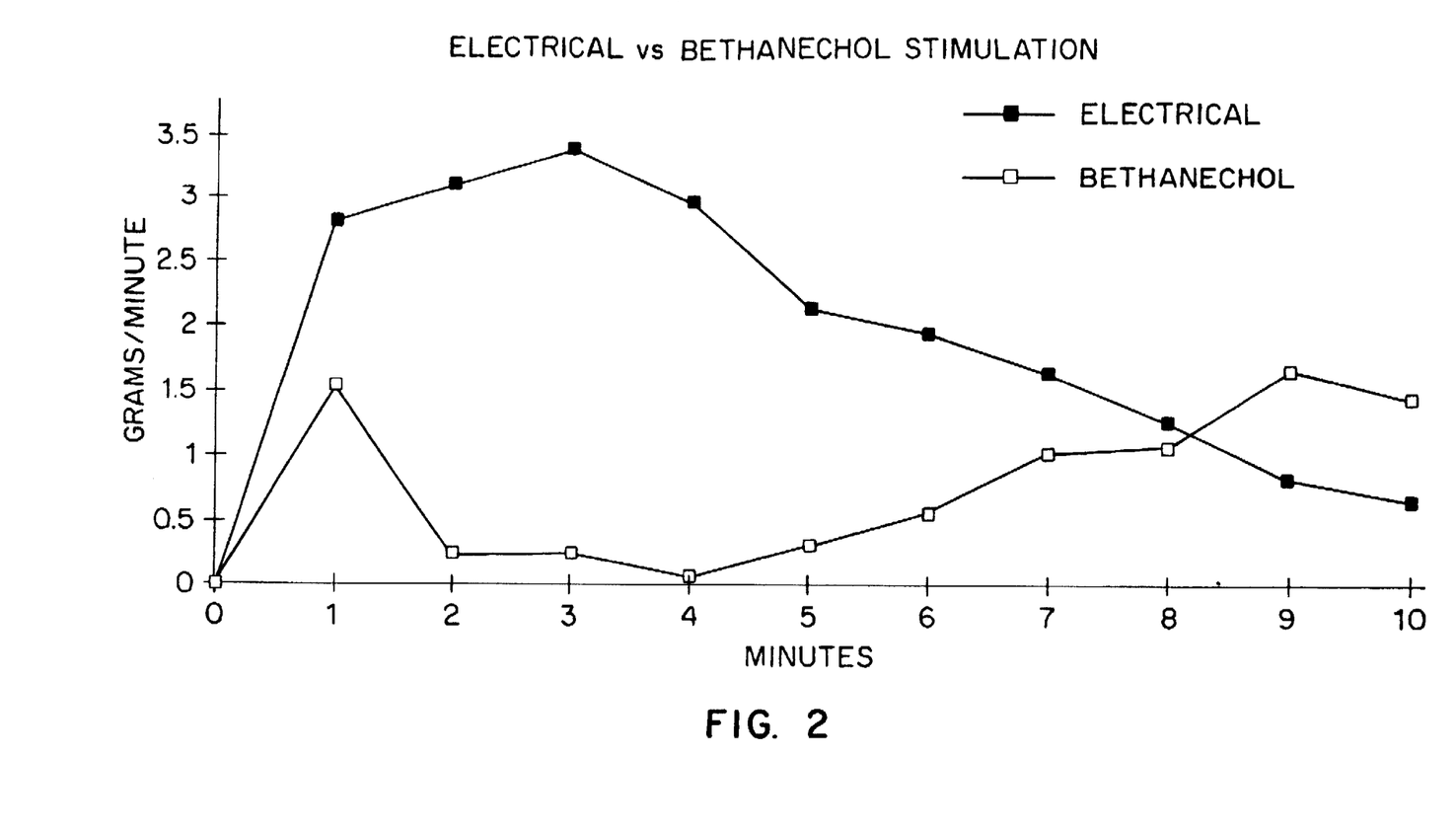
Figure 3:
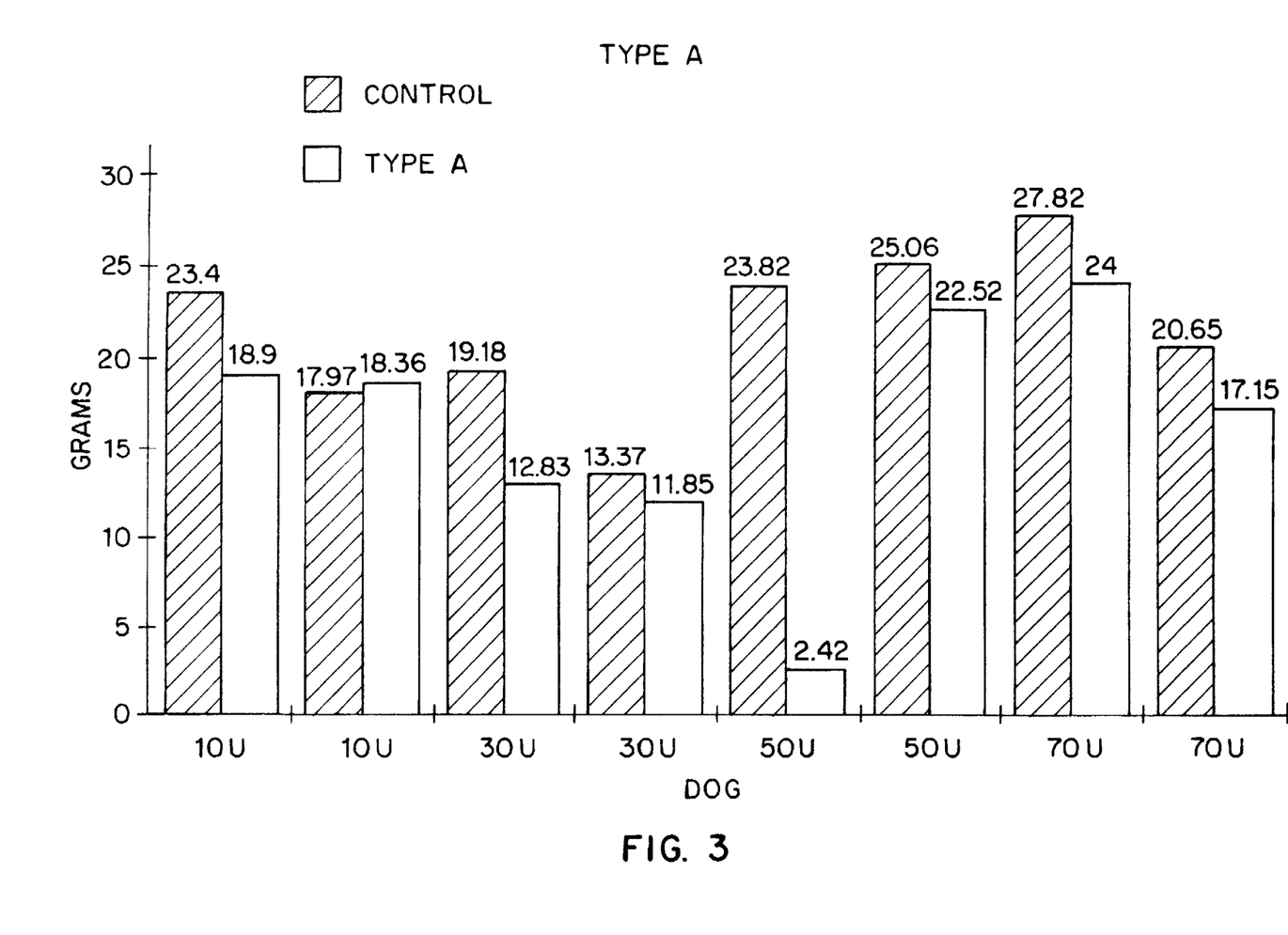
Figure 4:
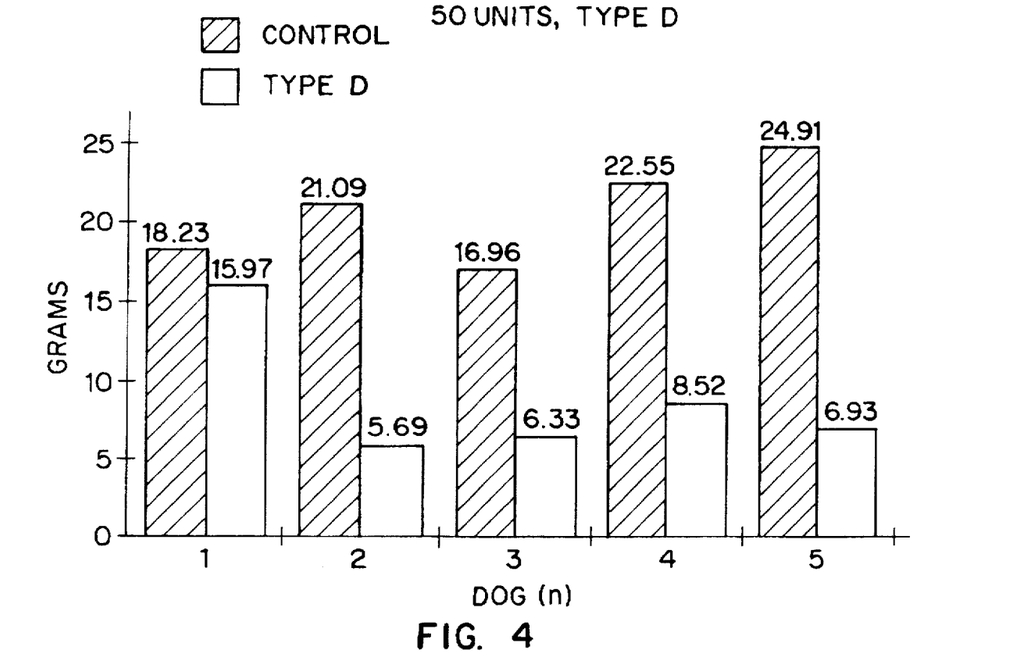
Figure 5:
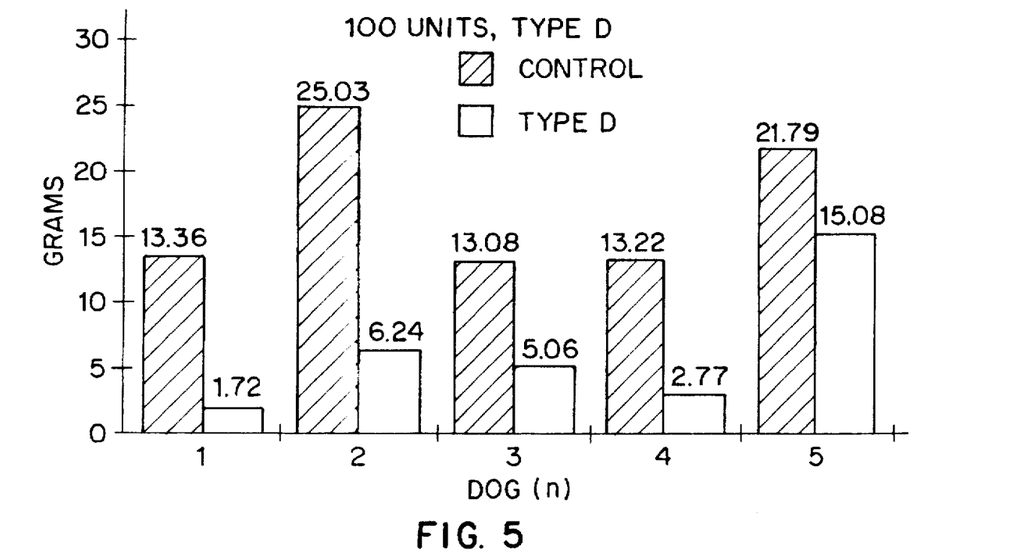
Figure 6A:
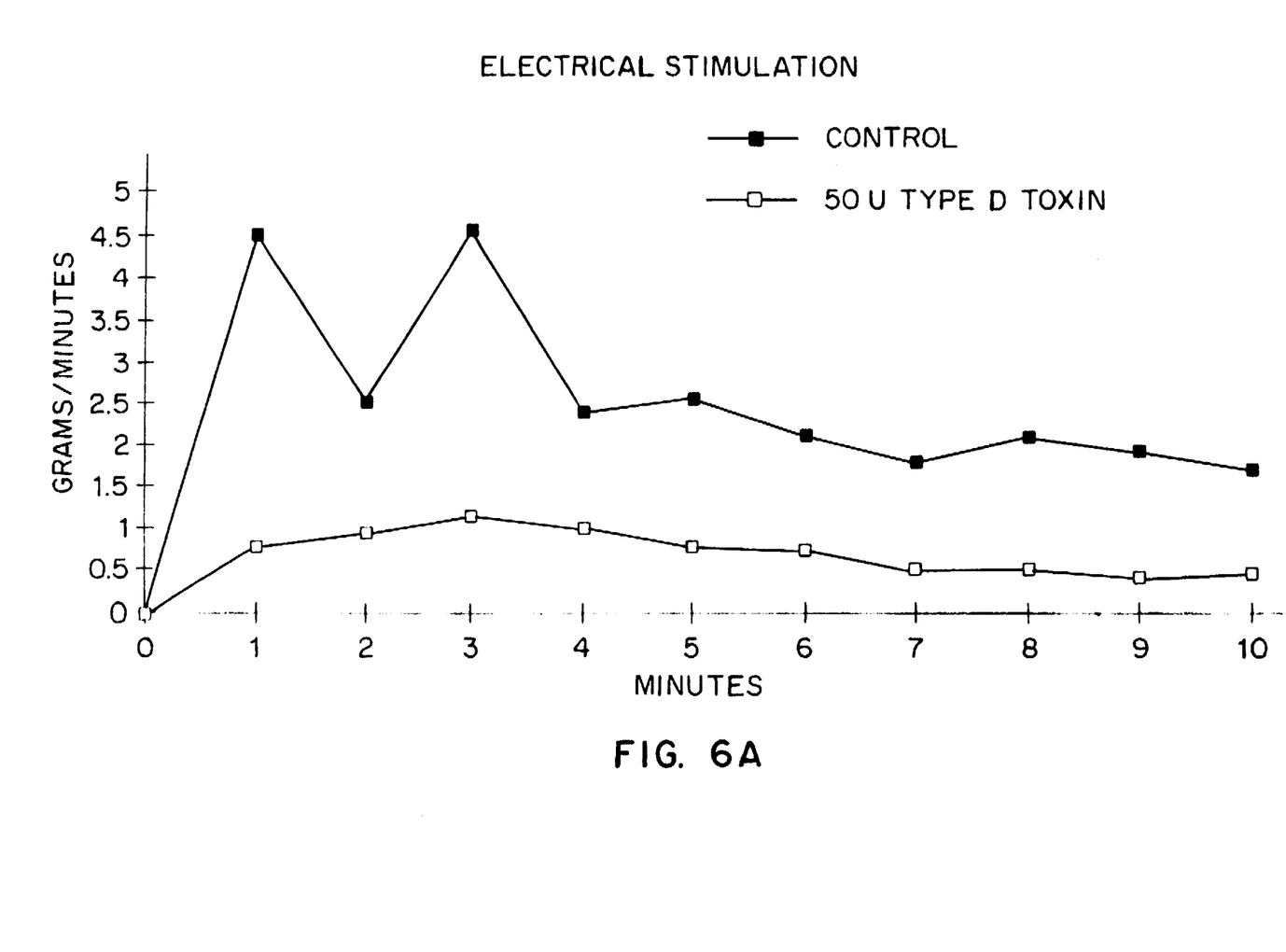
Figure 6B:
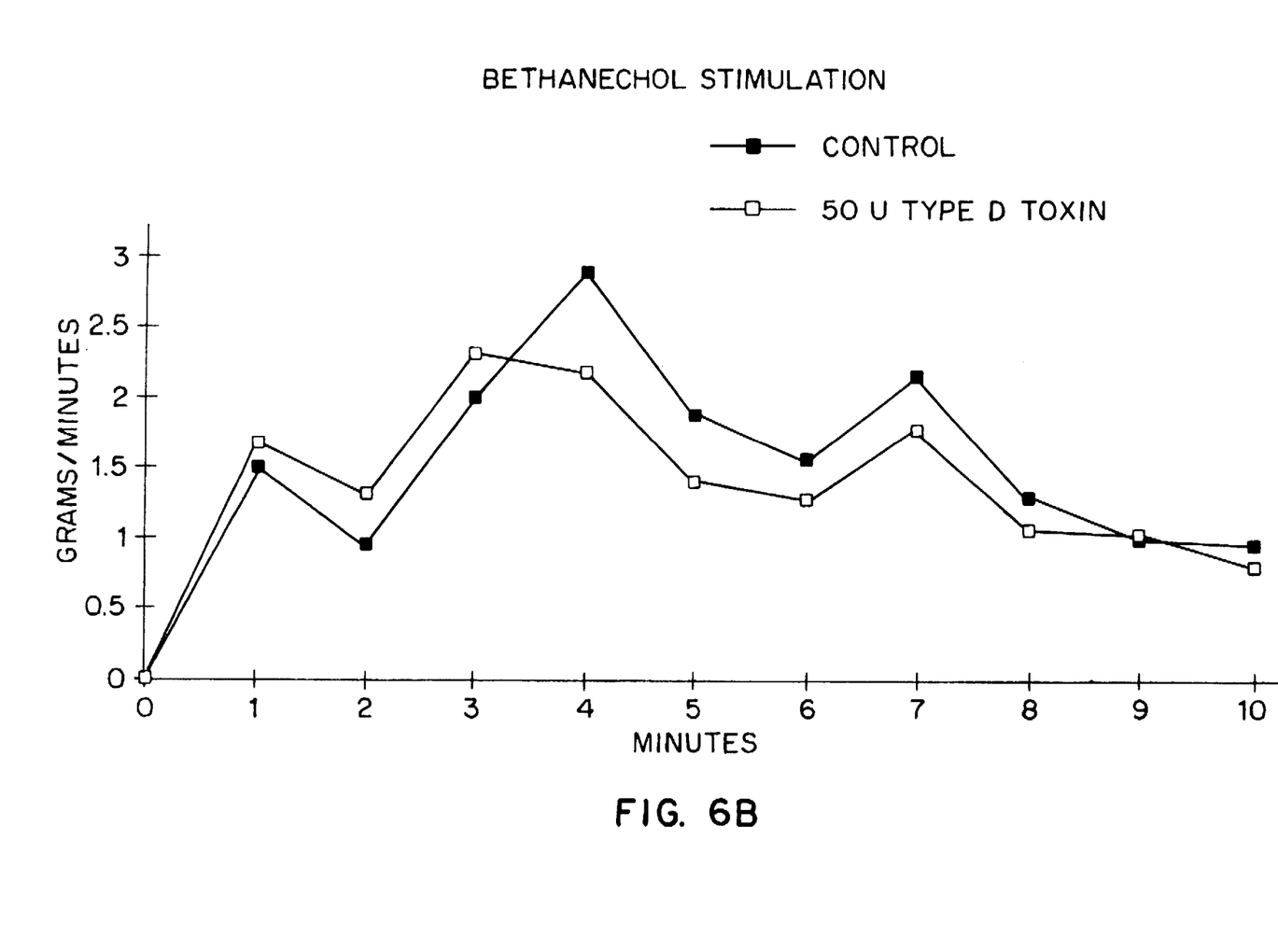
Figure 7:
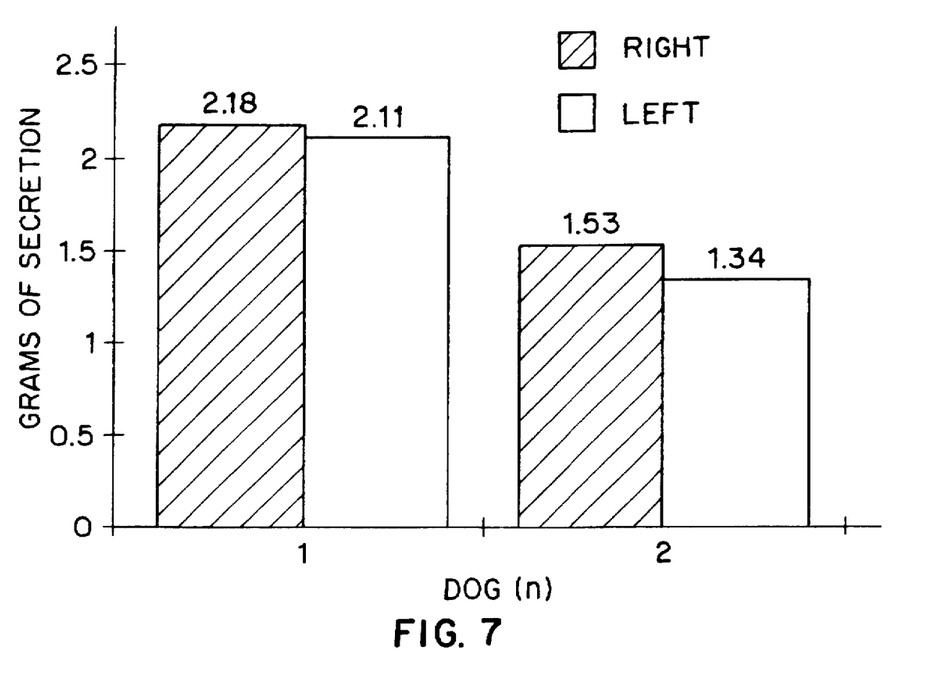

The results of the control study showed that equivalent stimulation of the right and left sphenopalatine ganglia of each dog produced nearly equivalent weights of nasal secretion. This is graphically represented in FIG. 7.

Figure 8:
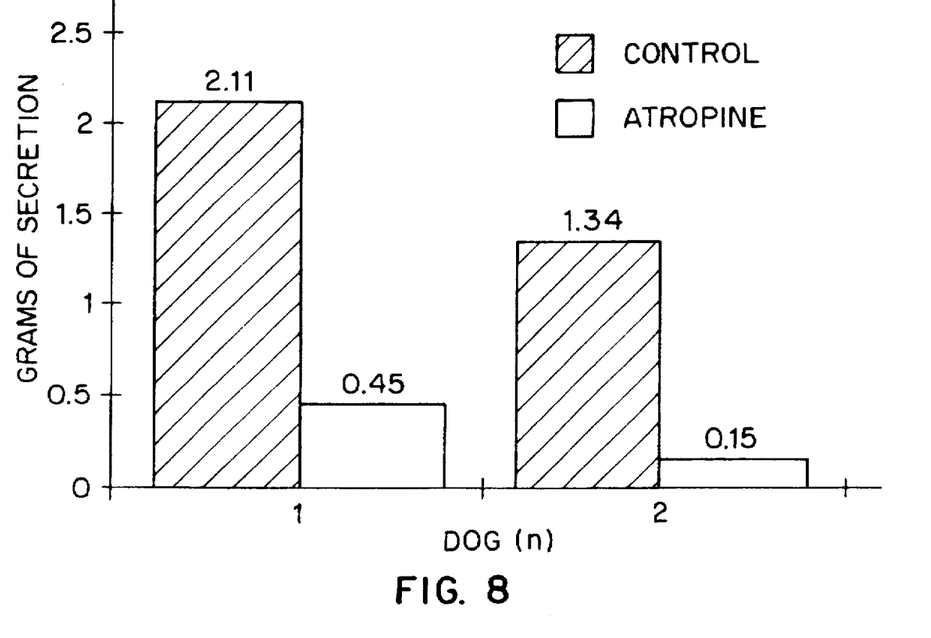

Systemic cholinergic blockade produced by intravenous atropine reduced the production of nasal secretion by 79% and 90% in two dogs. This is graphically represented in FIG. 8.

Figure 9:
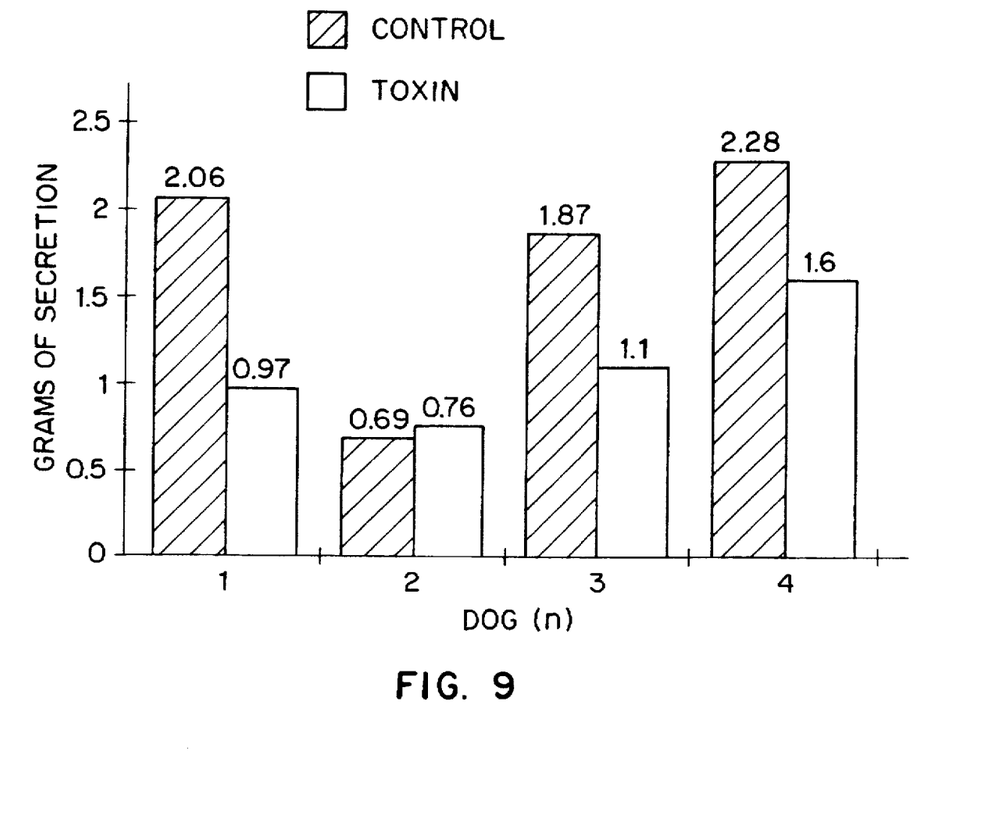

With respect to the effect to type A toxin, when compared to the saline-exposed nasal cavity, the botulinum-exposed nasal cavity showed a decreased weight of secretion in three of four dogs, but increased weight in one dog. Of the dogs showing a decreased secretion, the average decrease was 41% (specifically 53%, 41% and 30%). One dog showed a 10% increase in nasal secretion production. These results are summarized in FIG. 9.

The nasal neurosecretory pathways are complex, and merit brief discussion here. Sensation to the nasal mucosa is supplied by the trigeminal nerve (4). Topically anesthetizing the nasal mucosa relieves the sensation of nasal obstruction, but does not change nasopulomonary airway resistance (23).

The efferent nerve supply to the nasal mucosa consists of parasympathetic and sympathetic fibers (24). Preganglionic parasympathetic neurons leave the brainstem as the nervus intermedius. At the geniculate ganglion, some fibers continue anteriorly to become the greater petrosal nerve. This nerve enters the sphenopalatine ganglion to synapse with postganglionic parasympathetic neurons. Although acetylcholine is through to be the main neurotransmitter in the ganglion, VIP-containing cell bodies are also abundant (6). From here, parasympathetic fibers enter the sphenopalatine foramen to supply the vessels and glands of the nasal mucosa (4,25). Acetylcholine, VIP and the peptide PHI (25) are found in high concentrations in the nasal mucosa and may be the final mediators of parasympathetic nerve action (11). Although both glands and vessels have parasympathetic and sympathetic innervation, seromucinous secretion is controlled mainly by parasympathetic nerves, while vascular tone is controlled mainly by sympathetic nerves (26, 27). Mygind (8) noted that since the vascular, muscarinic cholino-ceptor is atropine resistant, the therapeutic potential for a nasal spray containing a choline-ceptor antagonist is limited to hypersecretion only (26).

Postganglionic sympathetic nerves enter the skull with the internal carotid artery. These fibers become the deep petrosal nerve and join the preganglionic parasympathetic nerves of the greater petrosal nerve in the pterygoid (Vidian) canal. Thus, the combination of postganglionic sympathetic nerves with preganglionic parasympathetic nerves constitutes the vidian nerve. These sympathetic nerve fibers follow their parasympathetic counterparts to supply vascular smooth muscle. The main function of sympathetic nerves is to regulate nasal airway resistance or patency (10).

It was demonstrated in Example I that botulinum toxin is capable of blocking autonomic secretomotor fibers in the canine submandibular gland. This example IV demonstrates that botulinum toxin exerts anticholinergic effect on the nasal mucosa as well. Three of four dogs exposed to botulinum type A toxin showed an average decrease of 41% of electrically-evoked rhinorrhea. This partial response is attributed to the fact that non-cholinergic neurotransmitters, such as VIP, may have been released following sphenopalatine ganglion stimulation. VIP contains potent secretory capabilities (11) and may not be blocked by botulinum toxin's anticholinergic effect. One dog demonstrated a paradoxical increase in nasal secretion when exposed to botulinum toxin. This may be because of a decreased sensitivity to toxin in this dog, or, more likely, because of failure to adequately stimulate the sphenopalatine ganglion on the control side.

One important difference between this example and the data from Example I relating to canine submandibular glands is that type A toxin showed a more potent anticholinergic effect in nasal mucosa when compared to salivary glands.

Injections of 10-70 units of type A toxin into eight canine submandibular glands reduced salivary production by an average of 19%. At present, there is no explanation for this difference, except to suggest that the nasal mucosa may be more densely innervated by parasympathetic nerves than the submandibular gland, or simply because the nasal mucosa is more sensitive to the toxin.

A further finding was that control dogs exposed to systemic atropine immediately prior to stimulation showed an 85% decrease in rhinorrhea. This greater decrease in rhinorrhea, when compared to botulinum-exposed mucosa, may be attributed to the fact that there was cholinergic blockage of the sphenopalatine ganglion in the atropinized dogs as well. Uddman (11) suggested that VIP fibers of the upper respiratory tract may originate from distal ganglia, which would not be affected by nasally-applied botulinum toxin, but may be blocked by systemic atropine. Therefore, sphenopalatine injections of toxin, which are fairly easy, may be very effective in human patients. Another possible explanation for the difference is that secretions generated from the paranasal sinuses following sphenopalatine ganglion stimulation were blocked by systemic atropine, but not by nasally-applied botulinum toxin. However, Tos (28) demonstrated that in humans, the gland density of the sinuses is extremely low and mucus producing capacity almost negligible.

Example V

Rhinorrhea in humans may be treated by administering botulinum toxin onto the nasal mucosa. The patient may be anesthetized and the nasal passage may be packed with gauzed soaked with a saline solution of botulinum toxin D (50 units/cc). Alternatively, the botulinum toxin may be injected into the sphenopalatine ganglion. Relatively long-term relief (e.g. up to six months) from chronic rhinorrhea is to be expected.

Example VI

Normal or excessive salivation may present problems in patients who have experienced cerebrovascular accidents, ALS, myasthenia gravis, bulbar palsy, or vagal dysfunction. Neurologically impaired patients may not be able to handle saliva secretions and may develop aspiration pneumonia. In order to block the parasympathetic nerve supply to the salivary glands, botulinum toxin is administered to the salivary glands of these patients by retrograde filling of the salivary ducts via the duct openings in the mouth. The same duct injection procedure can be followed as is presently used to inject radiopaque dyes into the salivary glands for radiographs of the ductal structure. All of the salivary glands can thus be "paralyzed" in a patient with four ductal injections.

Example VII

Patients with serous otitis media are treated by the transtympanic injection of botulinum toxin.

Example VIII

The relaxation of the bronchial muscles in asthmatic or COPD patients is accomplished by the administration of botulinum toxin. The toxin is delivered by means of a conventional aerosol inhaler. Alternatively, the toxin may be injected transbronchially.

Example IX

Excessive stomach acid secretion is treatable with botulinum toxin by oral ingestion of the toxin. Here it is contemplated that relatively dilute solutions (e.g. 10 unites/5 cc water ingested every 4-6 months), should provide relief.

Example X

Spastic colitis may be treated by administering botulinum toxin directly to the colon. This may be accomplished by administering 10 unites or more by enema or suppository. Again, the dosage frequency may be every 4-6 months.

Example XI

Persons who experience excessive and profuse sweating may obtain relief by the administration of botulinum toxin.

Ten units of the toxin may be injected intradermally in the area of the excessive sweating. The toxin might also be applied topically, e.g., 10 units mixed with a cream carrier.

It will be appreciated that in all instances of treatment of autonomic nerve function or dysfunction, the dosages of botulinum toxin may be varied within ranges already demonstrated to be safe for treatment of motor nerve disorders. Similarly, carriers, diluents, and means delivery known to be safe and effective, either for delivering botulinum toxin for motor nerve disorders, or for delivering other therapeutic agents to similar parts of the body, e.g. salivary glands, the stomach, nasal mucosa, etc., are contemplated.

Example XII

Spasms of the esophagus are treatable by injecting the toxin (e.g. 10 units) across the esophageal mucosa. Similar long term effects are contemplated such that treatment need only be undertaken once every several months.

We claim:

1. A method for the control of autonomic nerve function in a mammal comprising locally administering to cholinergic neurons of the autonomic system of the mammal an amount of botulinum toxin sufficient to cause denervation of the neurons, wherein said denervation results in control of autonomic nerve function in a target tissue or organ innervated by said neurons, wherein the autonomic nerve function includes the function of an autonomic nerve which contributes to at least one symptom of rhinorrhea, otitis media, excessive salivation, asthma, COPD, excessive stomach acid secretion, spastic colitis or excessive sweating.

2. A method for the alleviation of rhinorrhea in a mammal comprising locally administering botulinum toxin to the nasal cavity of the mammal in an amount sufficient to denervate cholinergic neurons of the autonomic nervous system that control mucous secretion in the nasal cavity.

3. A method for the alleviation of rhinorrhea in a mammal comprising topically administering botulinum toxin to the nasal mucosa in an amount sufficient to denervate cholinergic neurons of the autonomic nervous system that control mucus secretion into the nasal cavity.

4. A method for the alleviation of rhinorrhea in a mammal comprising injecting botulinum toxin into the sphenopalatine ganglion in an amount sufficient to denervate cholinergic neurons of the autonomic nervous system that control mucus secretion into the nasal cavity.

5. A method according to claim 1 for the treatment of otitis media comprising the transtympanic injection of botulinum toxin.

6. A method according to claim 1 for the treatment of excess salivation, comprising administering botulinum toxin to the salivary glands.

7. A method according to claim 6 wherein the mammal is a human afflicted with at least one of cerebrovascular accident, ALS, myasthenia gravis, bulbar palsy or vagal dysfunction.

8. A method according to claim 6 comprising administering botulinum toxin to the salivary glands by retrograde filling of the salivary ducts via the duct openings.

9. A method according to claim 1 for the treatment of the symptoms of asthma, comprising administering botulinum toxin to the bronchial tubes via an aerosol spray.

10. A method according to claim 1 for the treatment of the symptoms of asthma, comprising administering botulinum toxin to the bronchial tubes via an transbronchial injection.

11. A method according to claim 1 for decreasing stomach acid secretion, comprising orally ingesting a therapeutically effective amount of botulinum toxin.

12. A method according to claim 1 for alleviating spastic colitis, comprising enema injection into the colon of a therapeutically effective amount of botulinum toxin.

13. A method according to claim 1 for alleviating excessive sweating, comprising administering a therapeutically effective amount of botulinum toxin to the skin of a human.

14. A method according to claim 13, wherein the botulinum toxin is administered by intradermal injection.

15. A method according to any one of claims 1, 2, 3 and 4, wherein the botulinum toxin is at least one of botulinum toxins A, B, C, D, E, F or G.

16. A method according to claim 15, wherein the botulinum toxin is botulinum toxin A.

17. A method according to claim 15, wherein the botulinum toxin is botulinum toxin D.

18. A method according to any one of claims 1, 2, 3 and 4, wherein the botulinum toxin is defined as a toxin produced by *Clostridium butyricum* or *beratti*.

* * * * *

Adverse Decision In Interference

Patent No. 5,766,605, Ira Sanders, Christopher M. Shaari, TREATMENT OF AUTONOMIC NERVE DYSFUNCTION WITH BOTULINUM TOXIN, Interference No. 104,688, final judgment adverse to the patentees rendered February 26, 2002, as to claims 1 and 13-18.

*(Official Gazette March 26, 2002)*